United States Patent [19]

Webinger

[11] 4,402,433
[45] Sep. 6, 1983

[54] TWO PART CONTAINER WITH ADJUSTABLE VENTS

[75] Inventor: George Webinger, Minneapolis, Minn.

[73] Assignee: Champion International Corporation, Stamford, Conn.

[21] Appl. No.: 80,999

[22] Filed: Oct. 1, 1979

[51] Int. Cl.³ .............................................. B67D 3/00
[52] U.S. Cl. .................................................. 222/485
[58] Field of Search ............... 239/55, 58, 59, 60; 220/253, 256; 222/480, 481, 482, 484, 485, 545, 548, 553, 555, 565; 229/93, 4.5, 5.5, 5.6, 23 BT

[56] References Cited

U.S. PATENT DOCUMENTS

| 739,232 | 7/1903 | Stafford | 229/93 |
|---|---|---|---|
| 1,301,840 | 4/1919 | Hawkins | 229/4.5 |
| 1,711,642 | 5/1929 | Hulbert | 229/5.6 |
| 1,732,028 | 10/1929 | Reiner | 239/59 X |

FOREIGN PATENT DOCUMENTS 560143  3/1975  Switzerland ........................ 239/59

*Primary Examiner*—Allen N. Knowles
*Attorney, Agent, or Firm*—Evelyn M. Sommer; John H. Mulholland; William W. Jones

[57] ABSTRACT

A two part paperboard container having adjustable vents is described and is intended for use with a sublimable composition. The container consists of an inner tubular member and an outer tubular sleeve member, both of a truncated, conical configuration. The inner tubular member, which is adapted to receive the sublimable composition, is disposed within the outer sleeve member. The outer surface of the inner member is in frictional engagement with the inner surface of the outer sleeve member which functions to seal the carton. The inner member may be rotated relative to the outer sleeve member to at least partially align apertures provided in the upper cover portions of the tubular members, thereby exposing the composition to the air enabling it to sublime. Continued relative rotation of the tubular members will reset the apertures in the upper cover portions in a nonaligned position, thereby resealing the container. A handle means connected to a lower cover portion of the inner tubular member is provided to facilitate the relative rotation of the tubular members.

6 Claims, 6 Drawing Figures

TWO PART CONTAINER WITH ADJUSTABLE VENTS

The subject invention relates to a new and improved paperboard container having adjustable vents for use with a sublimable material such as an air freshener or insecticide. More particularly, the subject invention consists of a two part tapered tubular container, wherein the inner tube, containing the sublimable materials, is disposed within an outer tubular sleeve. The inner tubular member is frictionally engaged with the outer sleeve and is capable of rotation along its longitudinal axis relative to the outer sleeve. Die cut apertures or vents are provided in the generally circular upper cover portions of both the inner and outer tubular members. By rotating the inner member relative to the outer sleeve, the die cut apertures may be at least partially aligned such that the composition sealed within the inner member is exposed to the air, thereby enabling the composition to sublime. The sublimation process may be substantially reduced by further rotating the inner member to a position such that the respective die cut apertures in the upper cover portions are nonaligned, thereby resealing the composition within the tubes.

Prior art containers for sublimable materials are usually formed from a molded plastic material. The molded plastic material is provided with venting areas so that the sublimable material within the container can be exposed to .the air. These prior art containers are shipped from the manufacturer wrapped in a plastic material to prevent the unwanted and inadvertent sublimation of the product prior to use by the consumer. The consumer, wishing to use the product, unwraps the plastic material thereby exposing the sublimable product within the container to the air. Should the consumer wish to halt the sublimation of the product such that it may be used at a later time, it is necessary that the product be rewrapped in a plastic film. The rewrapping of the container is not only difficult, but in addition, forces the consumer to handle a potentially posionous composition.

Accordingly, it is an object of the subject invention to provide a container for sublimable material having adjustable vents for regulating the sublimation process.

It is another object of the subject invention to provide a container formed from a paperboard material, thereby reducing manufacturing costs.

It is a further object of the subject invention to provide a container having adjustable vents wherein the inner member can be rotated via a handle means disposed on the base of the inner member for controlling the rate of sublimation of the packaged material.

Accordingly, there is provided a two part paperboard container which consists of an inner tubular member and an outer tubular member of generally truncated, conical configuration. The inner tubular member is provided with a generally circular upper cover portion which has at least one die cut aperture therein. In a preferred embodiment, a plurality of generally triangular die cuts are provided in the upper cover portion and are disposed radially about the center of the cover portion. After insertion of a sublimable product within the inner member, the inner member is sealed by adhesively attaching a generally circular lower cover portion to the bottom edge thereof.

The outer sleeve member, also of generally truncated, conical configuration, has a diameter slightly larger than the diameter of the inner tubular member. The outer sleeve member is provided with an upper cover portion having at least one die cut aperture therein. In a preferred embodiment of the subject invention, the upper cover portion is provided with a plurality of generally triangular shaped die cut apertures arranged in substantially the same spatial relationship as the die cuts arranged in the upper cover portion of the inner sleeve member.

The inner tubular member is disposed within the outer sleeve member and a frictional engagement exists between the outer surface of the inner tubular member and the inner surface of the outer sleeve member, which thereby functions to seal the container. The outer tubular member is further provided with an upturned rolled edge which functions to hold the inner tubular member within the outer sleeve member and maintain the frictional engagement therebetween. A handle means is provided connected to the lower surface of the lower cover portion to facilitate the rotation of the inner member relative to the outer sleeve member. In a preferred embodiment, the handle means is additionally provided with an adhesive strip so that the container may be fastened at the point of use by the consumer.

The container may be shipped, stored and displayed in a sealed condition. More particularly, the respective die cuts in the upper cover portions are set in a non-aligned position which, in conjunction with the frictional engagement between the inner and outer tubular members, functions to seal the carton and prevent the inadvertent sublimation of the product. After purchasing the product, the consumer merely has to rotate the inner member relative to the outer sleeve member such that the respective die cuts in the upper cover portions are at least partially aligned thereby exposing the stored product to the air enabling it to sublime. In addition, should the consumer wish to substantially reduce or stop the sublimation process, he may again rotate the tubular members relative to each other until the die cut apertures do not overlap thereby resealing the sublimable material from the air.

Further objects and advantages of the subject invention will become apparent from the following detailed description, taken in conjunction with the drawings in which.

Figure 1:
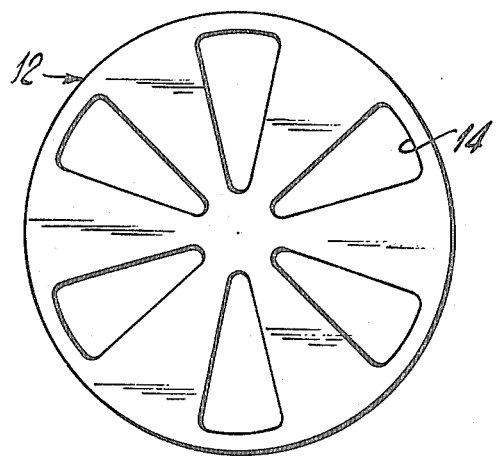
FIG. 1 is a plan view of the upper cover portion of the outer sleeve member of the container of the subject invention.
Figure 2:
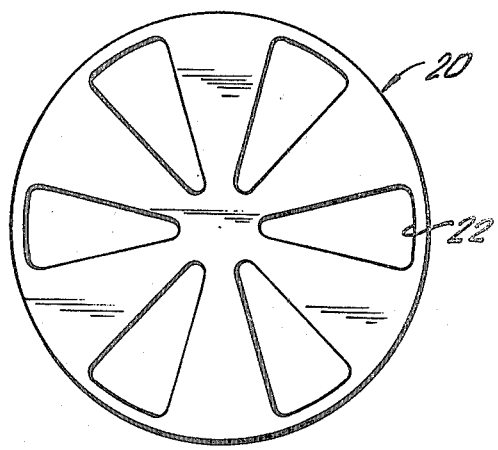
FIG. 2 is a plan view of the upper cover portion of the inner sleeve member of the container of the subject invention.

The generally circular upper cover portions of the subject invention, as illustrated in FIGS. 1 and 2, are formed from either a paperboard or plastic material. Outer upper cover portion 12, is of generally circular configuration and is provided with a plurality of generally triangular shaped die cut apertures 14 disposed radially about its center. Inner upper cover portion 20 is similarly provided with die cut apertures 22 disposed in substantially the same spatial relationship as the die cuts 14 of outer upper cover portion 12. Preferably, the die cuts 14 in upper cover portion 12 are at least as large as the die cuts 22 in upper cover portion 20 to permit sufficient ventilation. The diameter of the inner upper cover portion 20 is slightly less than the diameter of the outer upper cover portion 12 so that it will fit within the outer sleeve member 30 as more fully described hereinafter.

The container of the subject invention, indicated generally by the numeral 10, and as illustrated in FIGS. 3-6, is provided with a tubular outer sleeve member 30 of generally tapered truncated, conical configuration. An inner member 32 is also provided with a tapered truncated, conical configuration, and has a diameter slightly less than the diameter of outer sleeve member 30. In the formation of inner member 32, inner upper cover portion 20 is adhesively connected to the top edge 34 of inner member 32. A sublimable product (not shown) may then be inserted into the inner member 32. The product is sealed within inner member 32 by rolling the lower edge of inner member 32 inwardly, thereby forming an annular ring 38 extending perpendicularly inward from the sides of the inner member 32. A generally circular lower cover portion 40 may then be adhesively connected to annular ring 38, thereby sealing the sublimable product within the inner member 32.

In forming the outer sleeve member 30 of the container 10 of the subject invention, outer upper cover portion 12 is adhesively joined to the upper edge 42 of outer sleeve member 30. The container 10 is then formed by inserting inner member 32, containing the sublimable product, into the open bottom end of the outer sleeve member 30 until the upper surface of the inner upper cover portion 20 abuts the lower surface of the outer upper cover portion 12. Since the diameter of the inner member 32 is just slightly less than the diameter of the outer sleeve member 30, a frictional engagement is obtained between the outer surface of the inner member 32 and the inner surface of the outer sleeve member 30. By this arrangement, the product is sealed within container 10.

In order to maintain the positioning of the inner member 32 within the outer sleeve 30, the lower edge of the outer sleeve is upturned into a U-shaped, annular support member 50. By this arrangement, the bottom edge of the outer sleeve member 30 abuts and supports inner member 32, thereby maintaining its position within the outer sleeve member 30, and establishing the frictional engagement between the members 30, 32 which seals the carton. Since inner member 32 merely rests on support member 50, relative rotation of the members 30, 32 is not inhibited. Alternatively, a plastic ring or other such device may be substituted for support member 50 in order to maintain inner member 32 within outer member 30.

Inner member 32 is rotatable about its longitudinal axis relative to outer sleeve member 30. To facilitate the rotation of the inner member 32 relative to outer sleeve member 30, a handle 52 is adhesively connected to lower cover portion 40. Handle 52 is generally square in configuration and may be formed from a plastic foam or other similar material. Handle 52 can be readily grasped and rotated which in turn causes the rotation of inner member 32 relative to outer member 30. In a preferred embodiment, the bottom of handle 52 further includes an adhesive portion 54 covered by a protective strip 56. By this arrangement, the consumer, by peeling back protective strip 56 and exposing the adhesive section 54, may fixedly attach the container 10 to a wall, ceiling or an article of furniture during its use.

Figure 3:
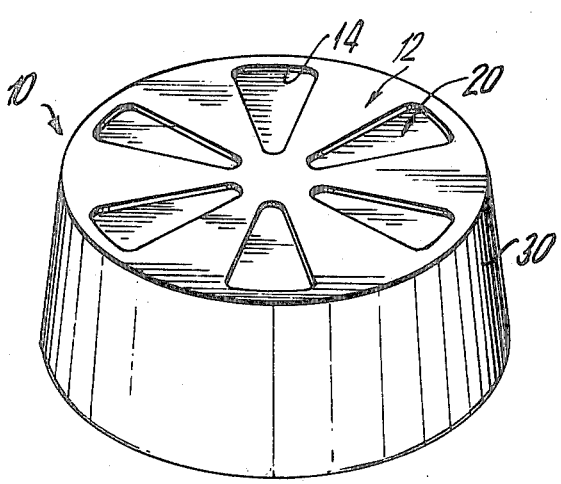
FIG. 3 is a perspective view of the erected container of the subject invention illustrating the closed position of the vents.
Figure 4:
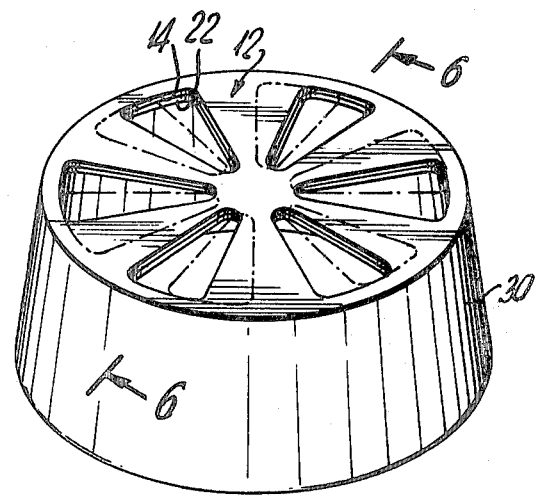
FIG. 4 is a perspective view similar to FIG. 3 illustrating the open position of the vents.
Figure 5:
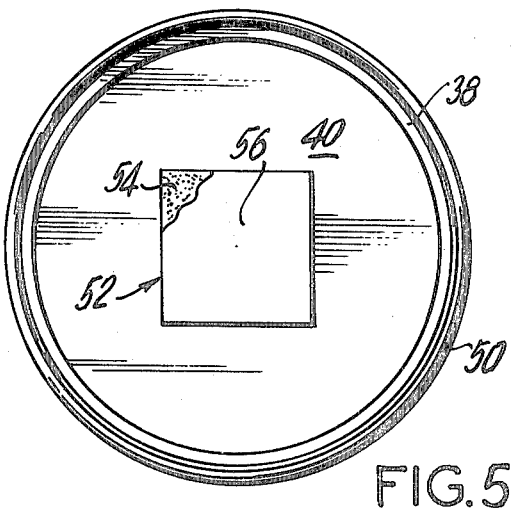
FIG. 5 is a plan view of the bottom of the container of the subject invention.
Figure 6:
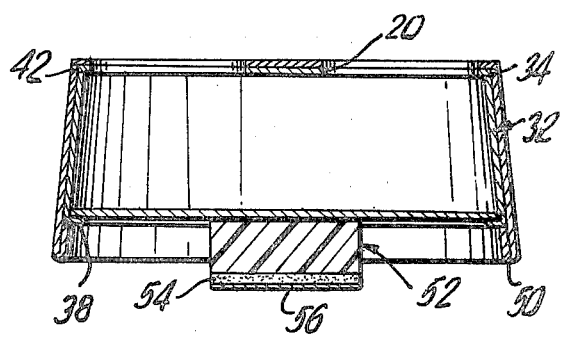
FIG. 6 is a cross sectional view of the container of the subject invention taken along line 6—6 in FIG. 4.

When the container 10 of the subject invention is shipped, stored and displayed, the die cuts 14 and 22 are in a nonaligned position thereby sealing the container as more particularly illustrated in FIG. 3. At a time when the consumer wishes to start the sublimation process, he merely has to grasp handle 52 and rotate inner member 32 relative to outer sleeve member 30 thereby at least partially aligning die cuts 14 and 22 of the upper cover portions 12 and 20. As more particularly illustrated in FIG. 4, the die cuts may be either fully or partially aligned (as indicated by the dotted line) such that the rate of sublimation of the product can be regulated. Should the consumer wish to halt the sublimation process, he merely has to further rotate the inner member 32 relative to the outer member 30 such that the die cuts 14, 22 will again be in the nonaligned position and will thereby reseal the carton and substantially reduce the sublimation process.

Accordingly, there is provided a new and improved two part container having adjustable vents for use with a sublimable material. The container consists of an inner member and an outer sleeve member of generally tapered, truncated, conical configuration. The inner member is provided with a circular upper cover portion having a plurality of die cut apertures therein and adhesively attached to the upper edge of the inner member. The inner member is adapted to receive a sublimable product which is then sealed within the inner member. The outer sleeve member is similarly provided with an upper circular cover portion having die cut apertures of substantially the same configuration and spatial arrangement as the die cut apertures found in the upper cover portion of the inner member. The inner member, disposed within the outer sleeve member, is frictionally engaged therewith and is capable of rotation along its longitudinal axis relative to the outer sleeve member. The die cuts of the inner and outer members may be at least partially aligned by rotating the inner member relative to the outer sleeve, thereby exposing the composition sealed within the inner member to the air enabling the composition to sublime. The sublimation process may be reduced by further rotating the inner member to a position wherein the respective vents in the upper cover portions are not aligned, thereby resealing the product within the container. In addition, a handle is provided which is adhesively attached to the inner sleeve member to facilitate the rotation of the inner member relative to the outer sleeve member.

Although the subject carton has been described by reference to preferred embodiments, it is apparent that other modifications could be devised by those skilled in the art that would fall within the scope and spirit of the present invention as defined by the appended claims.

What is claimed is:

1. A two part paperboard container having adjustable vents, for holding a solid sublimable composition comprising:

an inner tubular memer of generally truncated, conical configuration, said inner tubular member having a generally circular inner upper cover portion adhesively and irremovably joined to the upper end thereof, said inner upper cover portion being provided with at least one die cut aperture therein, said inner tubular member being adapted to receive said solid composition;

means for sealing the lower end of said inner tubular member;

an outlet tubular sleeve member of generally truncated, conical configuration, said outer sleeve member having a diameter larger than the diameter of said inner member, said outer sleeve member including a generally circular outer upper cover portion, said outer upper cover portion being provided with at least one die cut aperture therein at least as large as the die cut aperture of the inner upper cover member; said inner tubular member being disposed within said outer sleeve member; said members being capable of relative rotation therein about the longitudinal axes of said members;

means for facilitating the relative rotation of said tubular members; and means for holding said inner tubular member within said outer sleeve member such that a frictional enagement is obtained between the outer surface of said inner tubular member and the inner surface of said outer sleeve member, and such that the upper surface of said inner upper cover portion abuts the lower surface of said outer upper cover portion whereby when said inner tubular member is rotated relative to said outer sleeve member, the die cut apertures of the upper cover portions of the respective tubular members are relatively movable from a position in which they do not register through partially aligned positions to a fully registered position and back toward the non-registering position such that the solid composition within said inner tubular member is exposed to the air, thereby enabling the composition to sublime;

said means for holding said inner tubular member within said outer sleeve member comprising an annular support member formed from rolling the bottom edge of said outer sleeve member into an upturned U-shaped configuration such that the bottom edge of said inner tubular member rests on the upturned bottom edge of said outer sleeve member and is supported thereby and in frictional air-excluding relation therewith.

2. A two part paperboard container as recited in claim 1 wherein said upper cover portions are provided with a plurality of generally triangular die cut apertures which radially extend from the center of said portions.

3. A two part paperboard container as recited in claim 1 wherein the means for sealing the lower end of said inner tubular member includes an annular ring formed by rolling the lower edge of said inner member perpendicularly inward, said means further including a generally circular lower cover portion adhesively joined to said annular ring thereby sealing the inner member.

4. A two part paperboard container as recited in claim 3 wherein the means for facilitating the relative rotation of said tubular members includes a handle adhesively connected along one side thereof to said lower cover portion of said inner member.

5. A two part paperboard container as recited in claim 4 wherein the opposed side of said handle is provided with an adhesive surface covered by a protective strip such that when said protective strip is removed the container may be adhesively connected to a substrate along said adhesive surface.

6. A two part paperboard container having adjustable vents, for holding a solid sublimable composition comprising:

an inner tubular member of generally truncated, conical configuration, said inner tubular member having a generally circular inner upper cover portion adhesively and irremovably joined to the upper end thereof, said inner upper cover portion being provided with a plurality of generally triangularly shaped die cut apertures which radially extend from the center of said inner upper cover portion, said inner tubular member including an annular ring formed by rolling the lower edge of said inner member perpendicularly inward, said inner tubular member further including a generally circular lower cover portion adhesively joined to said annular ring, said inner tubular member being adapted to receive said solid composition;

an outer tubular sleeve member of generally truncated, conical configuration, said outer sleeve member having a diameter larger than the diameter of said inner member, said outer sleeve member including a generally circular outer upper cover portion, said outer upper cover portion being provided with a plurality of generally triangularly shaped die cut apertures which radially extend from the center of said outer upper cover portion, said die cut apertures in said outer upper cover portion being at least as large as the die cut apertures in said inner upper cover portion, with said inner tubular member being disposed within said outer sleeve member and capable of rotation therein about the longitudinal axis of said members, said outer sleeve member further including an annular support member formed from rolling the bottom edge of said outer sleeve member into an upturned U-shaped configuration such that the bottom edge of said inner tubular member rests on the upturned bottom edge of said outer sleeve member and is supported thereby such that a frictional engagement is obtained between the outer surface of said inner tubular member and the inner surface of said outer sleeve member and such that the upper surface of said inner upper cover portion abuts the lower surface of said outer upper cover portion; and a handle adhesively connected to said lower cover portion of said inner member, said handle for facilitating the relative rotation of said tubular members whereby when said inner tubular member is rotated relative to said outer sleeve member, the die cut apertures of the upper cover portions of the respective tubular members may be at least partially aligned such that the solid composition within said inner tubular member is exposed to the air thereby enabling the composition to sublime.

* * * * *